United States Patent [19]

Tanaka et al.

[11] Patent Number: 5,271,816
[45] Date of Patent: Dec. 21, 1993

[54] OXYGEN SENSOR

[75] Inventors: Hiroshi Tanaka, Aichi; Masashi Tanaka, Takatsuki; Shigekazu Yamauchi, Nagaokakyo; Masaru Fukunaga, Kyoto, all of Japan

[73] Assignee: Mitsubishi Jidosha Kogyo Kabushiki Kaisha, Tokyo, Japan

[21] Appl. No.: 815,582

[22] Filed: Dec. 30, 1991

Related U.S. Application Data

[63] Continuation of Ser. No. 433,547, Nov. 8, 1989, abandoned.

[30] Foreign Application Priority Data

Nov. 18, 1988 [JP] Japan .............. 63-149761[U]
Jun. 9, 1989 [JP] Japan ................ 1-66689[U]

[51] Int. Cl.$^5$ ............................................. G01N 27/417
[52] U.S. Cl. ...................................... 204/153.16; 204/427; 204/428; 204/429
[58] Field of Search .................. 204/428, 429, 427; 502/174, 319, 338

[56] References Cited

U.S. PATENT DOCUMENTS

| | | | |
|---|---|---|---|
| 2,709,159 | 5/1955 | Daussat | 502/338 X |
| 4,132,615 | 1/1979 | Linder et al. | 204/428 |
| 4,151,060 | 4/1979 | Isenberg | 204/428 |
| 4,199,425 | 4/1980 | Sinkevitch | 204/429 |
| 4,212,273 | 7/1980 | Maruoka | 123/438 |
| 4,233,142 | 11/1980 | Rohr et al. | 204/429 |
| 4,362,605 | 12/1982 | Bozon et al. | 204/1 T |
| 4,540,563 | 9/1985 | Chinchen | 502/338 X |
| 4,552,750 | 11/1985 | van der Wal et al. | 502/338 X |
| 4,598,062 | 7/1986 | Schneider et al. | 502/338 X |

FOREIGN PATENT DOCUMENTS

| | | | |
|---|---|---|---|
| 212180 | 7/1956 | Australia | 502/338 |
| 746909 | 8/1970 | Belgium | 502/338 |
| 3223656 | 1/1983 | Fed. Rep. of Germany . | |
| 3343405 | 6/1984 | Fed. Rep. of Germany . | |
| 3518192 | 11/1986 | Fed. Rep. of Germany . | |
| 2937802 | 2/1987 | Fed. Rep. of Germany . | |
| 3743435 | 7/1988 | Fed. Rep. of Germany . | |
| 90256 | 7/1981 | Japan . | |

*Primary Examiner*—Donald R. Valentine
*Assistant Examiner*—William T. Leader

[57] ABSTRACT

An oxygen sensor includes a hollow tubular element made of a solid electrolyte capable of conducting oxygen ions. The inner surface of the element is exposed to the atmosphere, and the outer surface thereof is exposed to an exhaust gas of which the oxygen concentration is to be detected. First and second electrodes are arranged on the inner and outer surfaces of the element, respectively. The second electrode is provided with a coating which contains a catalyst for causing and promoting a water gas reaction of carbon monoxide contained in the exhaust gas approaching the second electrode. Alternatively, a large number of pellets containing the catalyst are charged in the space between the tubular element and a protective tube surrounding the element.

7 Claims, 3 Drawing Sheets

OXYGEN SENSOR

This application is a continuation of application Ser. No. 07/433,547 filed on Nov. 8, 1989, now abandoned.

BACKGROUND OF THE INVENTION

This invention relates to an oxygen sensor for detecting a concentration of oxygen contained in an exhaust gas of a motor vehicle, to control, for example, the air-fuel ratio of a mixture supplied to the vehicle engine.

Conventionally, oxygen sensors are used to control the air-fuel ratio for motor vehicles. Oxygen sensors of this type comprise an element which is made of a solid electrolyte capable of conducting oxygen ions and which has a first surface exposed to a reference gas having a constant concentration of oxygen, usually the atmosphere, and a second surface exposed to a gas of which the oxygen concentration is to be detected, i.e., the exhaust gas of a motor vehicle. The first and second surfaces are respectively provided with first and second porous electrodes both having gas permeability. Thus, the oxygen sensor forms a so-called concentration cell.

During operation of the oxygen sensor, when the concentration of oxygen contained in the exhaust gas, i.e., the partial pressure of oxygen, becomes substantially 0, that is, when the air-fuel ratio of a mixture supplied to the vehicle engine becomes smaller than the stoichiometric ratio and thus enriches the mixture, a large electromotive force is produced between the first and second electrodes of the oxygen sensor. Therefore, by detecting the voltage produced between the first and second electrodes, it is possible to determine whether or not the air-fuel ratio of the mixture is equal to the stoichiometric ratio, namely, whether the mixture is rich or lean. As a result, the air-fuel ratio of the mixture can be maintained at the stoichiometric ratio by controlling the quantity of fuel supplied to the engine from a fuel supply device in accordance with a voltage signal from the oxygen sensor.

When the air-fuel ratio of the mixture is equal to the stoichiometric ratio, the amount of carbon monoxide (CO) and hydrocarbon (HC) and the amount of nitrogen oxides (NOx) contained in the exhaust gases are small. This ratio is desirable for reducing of air pollution.

The above-mentioned conventional oxygen sensors are generally poor in responding to oxygen concentration changes, and are particularly disadvantageous, when the air-fuel ratio of the mixture changes to a lean (higher) side from a rich (lower) side after acceleration or high-load operation of a vehicle, because such a change to the lean side cannot be quickly detected. As the mixture becomes rich, the amount of carbon monoxide in the exhaust gas increases and the amount of carbon monoxide that is absorbed into the electrode exposed to the exhaust gas is increased, whereby the exhaust gas-side electrode is poisoned by carbon monoxide, If the electrode is poisoned, molecules of oxygen which are contained in the exhaust gas, cannot reach the electrode quickly enough. In such a case, when the air-fuel ratio of the mixture changes to a lean side, the oxygen sensor remains temporarily unable to detect such a change.

If a delay occurs in the detection of oxygen concentration in an exhaust gas by the oxygen sensor, as mentioned above, the fuel supply device erroneously adjusts an amount of the fuel supplied to the engine so that the air-fuel ratio of the mixture is further changed to a lean side. As a result, an excess of oxygen molecules exist in the exhaust gas and the temperature of the exhaust gas rises. Furthermore, a so-called lean spike occurs and the amount of nitrogen oxides in the exhaust gas increases.

OBJECTS AND SUMMARY OF THE INVENTION

An object of the present invention is to provide an oxygen sensor capable of reliably guiding oxygen molecules contained in a gas, which is being detected, to an electrode exposed to the gas. Thus the responsiveness of the sensor to changes in the oxygen concentration of the gas is improved. More particularly, an oxygen sensor, which is able to detect the oxygen concentration of an exhaust gas from an engine of a motor vehicle is provided for controlling the air-fuel ratio of a mixture supplied to the engine.

The above object is achieved by an oxygen sensor of the present invention which comprises: an element made of a solid electrolyte capable of conducting oxygen ions, the element including a first surface exposed to a reference gas having a constant oxygen concentration, and a second surface exposed to a gas to be detected; electrode means for obtaining an electromotive force produced between the first and second surfaces due to a difference in the oxygen concentration between the detected gas and the reference gas, the electrode means including a first electrode arranged on the first surface of the element and a second electrode arranged on the second surface of the element and catalyst means for causing and promoting a water gas reaction relative to the carbon monoxide contained in the detected gas approaching the second electrode.

According to the above oxygen sensor, if carbon monoxide is contained in the detected gas approaching the second electrode, the carbon monoxide is subjected to the water gas reaction by the catalyst means to form carbon dioxide. Accordingly, formation of a carbon monoxide film on the second electrode due to the absorption of carbon monoxide can be avoided. Thus, oxygen molecules in the detected gas can reach the second electrode without being hindered so that the responsiveness of the oxygen sensor relative to changes in the oxygen concentration of the gas is improved.

When using the oxygen sensor of the present invention to detect the oxygen concentration of an exhaust gas of a motor vehicle, the sensor can quickly detect a change in the air-fuel ratio of a mixture supplied to the vehicle engine even when the change is from a rich side to a lean side. Accordingly, the above-mentioned lean spike can be avoided and the amount of nitrogen oxides in the exhaust gas can be reduced.

An example of the aforesaid catalyst means includes a coating which is formed on a surface of the second electrode. The coating is capable of passing oxygen molecules therethrough, and contains a catalyst for promoting the water gas reaction.

Another example of the catalyst means includes a protective cover for externally covering the second surface of the aforesaid element. The protective cover has a large number of small holes which allows the gas to be to pass therethrough, and a large number of pellets charged in the space between the protective cover and the element. These pellets contain a substance for providing a catalytic action to promote the water gas reaction.

BRIEF DESCRIPTION OF THE DRAWINGS

The present invention, together with its objects and advantages, will become more fully understood from the detailed description given herein below and the accompanying drawings, which are given by way of illustration only, and thus, are not limitative of the present invention, and wherein.

DETAILED DESCRIPTION OF THE PREFERRED EMBODIMENT

Figure 1:
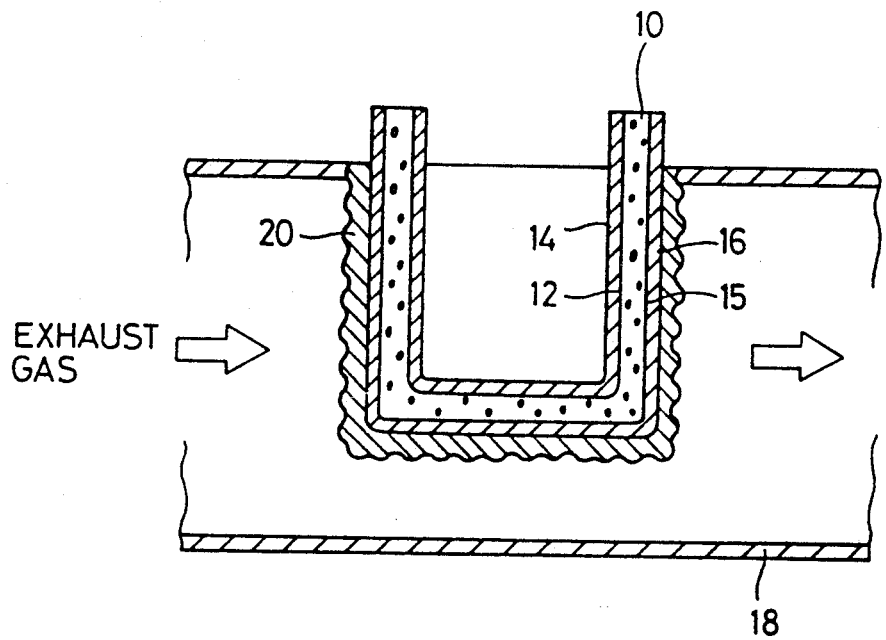
FIG. 1 is a schematic sectional view of an oxygen sensor according to a first embodiment of this invention.

An oxygen sensor illustrated in FIG. 1 is used to detect the oxygen concentration of an exhaust gas from a motor vehicle, and comprises a hollow tubular element 10 which is closed at one end and open at the other end. The hollow element 10 is made of a solid electrolyte capable of conducting oxygen ions, for example, yttria stabilized zirconia.

The hollow element 10 has an inner surface 12 provided with a first electrode 14, and an outer surface 15 provided with a second electrode 16. The first and second electrodes 14 and 16 are in the form of a layer covering substantially the entire areas of the inner and outer surfaces 12 and 15, respectively, and are made of porous platinum (Pt) in order to be permeable to gases.

The first and second electrodes 14 and 16 are connected to a voltage detecting circuit (not shown), which detects a voltage produced between the first and second electrodes 14 and 16, i.e., an electromotive force corresponding to the oxygen concentration of the exhaust gas. More specifically, a voltage signal from the voltage detecting circuit is, though not illustrated, supplied to a control circuit of a fuel supply device which supplies fuel to the engine of a motor vehicle, and, in accordance with the voltage signal, the control circuit controls the quantity of fuel supply, i.e., the air-fuel ratio of a mixture supplied to the engine.

The oxygen sensor is arranged in the middle of an exhaust pipe 18 extending from the engine, as illustrated in FIG. 1, so that an electromotive force corresponding to the oxygen concentration of the exhaust gas is produced between the first and second electrodes 14 and 16, as mentioned above. Specifically, the oxygen sensor is mounted to the exhaust pipe 18 such that the closed end and open end of the element 10 are projected into and out from the exhaust pipe 18, respectively.

Figure 5:
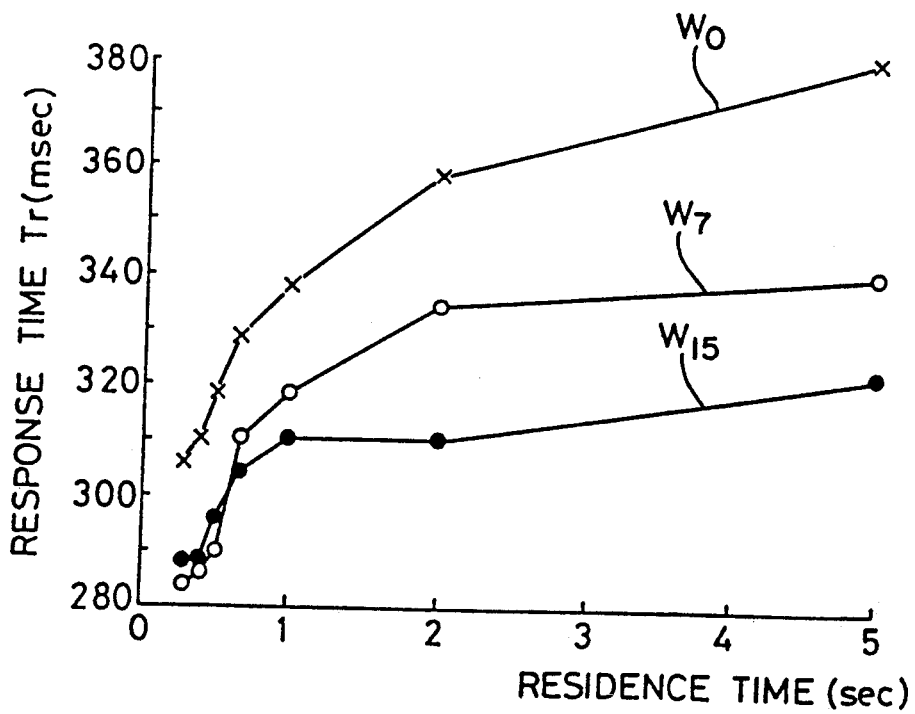
FIG. 5 is a graph illustrating the relationship between the content of water in a gas to be detected and the response time of the oxygen sensor when the gas to be detected is an exhaust gas of a motor vehicle.

The oxygen sensor of the present embodiment prevents carbon monoxide contained in an exhaust gas from being absorbed to the surface of the second electrode 16. To better explain this embodiment of the invention, one of the experiments conducted by the inventors for preventing carbon monoxide from being absorbed will now be described. In this experiment, the response time of the oxygen sensor required for detecting the oxygen concentration of an exhaust gas whose water content was changed in different ratios, more specifically, the response time of the oxygen sensor relative to a change of the air-fuel ratio of a mixture from a rich side to a lean side, was measured, and the time varied for which the enriched state of the mixture was maintained, i.e., the residence time. FIG. 5 illustrates the result of this experiment, wherein the residence time is indicated along the axis of abscissa and the response time Tr of the oxygen sensor is indicated along the axis of ordinate. In FIG. 5, a characteristic curve W0 illustrates the case of an exhaust gas containing 0% water, a characteristic curve W7 illustrates the case of an exhaust gas containing about 7% water, and a characteristic curve W15 illustrates the case of an exhaust gas containing about 15% water.

As is clear from FIG. 5, when the water content of the exhaust gas increases, the response time Tr of the oxygen sensor becomes shorter, without regard to the time for which the enriched state is maintained.

This is presumably because, when water is contained in the exhaust gas, a water gas reaction expressed by the following formula occurs near the surface of the exhaust gas-side electrode, i.e., the second electrode 16.

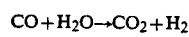

$$CO + H_2O \rightarrow CO_2 + H_2$$

If such a water gas reaction occurs, the amount of carbon monoxide which reaches or is absorbed to the surface of the second electrode 16 is decreased, whereby formation of a carbon monoxide film on the surface of the second electrode 16 is avoided.

As a result, oxygen molecules in the exhaust gas can reach the surface of the second electrode 16 without being hindered. Accordingly, the response time Tr of the oxygen sensor can be shortened.

For this reason, the oxygen sensor of this embodiment of the invention is provided with a coating 20 formed on the surface of the second electrode 16 which is exposed to an exhaust gas from being preventing carbon monoxide in the exhaust gas from being absorbed to this surface of the second electrode 16. The coating 20 is permeable to the exhaust gas and contains a substance which causes a catalysis to promote the water gas reaction expressed by the aforesaid formula.

Among catalysts providing such a catalytic action, the catalysts containing ferric oxide ($Fe_2O_3$) as a major component which are added to with one or two kinds of promoters, for example, are useful. The promoters to be added may be chromium oxide ($Cr_2O$) and potassium carbonate ($K_2CO_3$), or other substances. It is known that these two promoters both may serve to activate the catalysis of ferric oxide and, by adding both the promoters to ferric oxide, the catalysis of ferric oxide can be further activated due to a synergistic effect. As the promoters, metal oxides including cobalt (Co), nickel (Ni), copper (Cu) or lead (Pb) are useful, but these metal oxides combine with sulfur (S) in exhaust gases to form a toxic substance and therefore must be used carefully.

The coating 20 on the surface of the second electrode 16 can be produced, for example, by adding powder of the catalyst and promoters to powder of heat-resistant inorganic materials such as spinel, silica, alumina, etc., preparing a paste of the mixture, applying the paste to the surface of the second electrode 16, followed by baking that surface of the second electrode 16.

Figure 2:
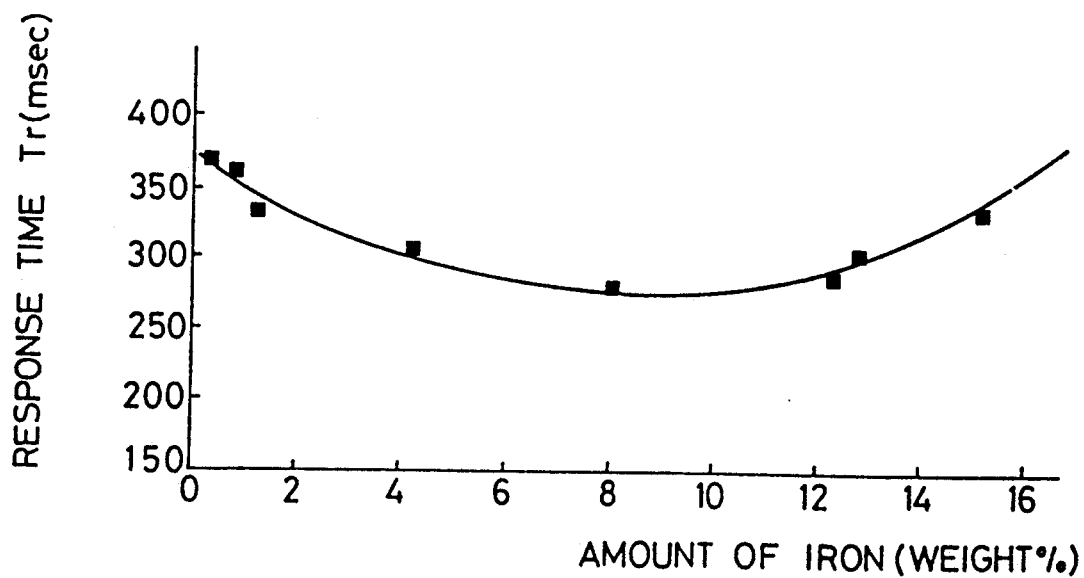
FIG. 2 is a graph illustrating the relationship between the amount of a catalyst contained in a coating of a second electrode as illustrated in FIG. 1 and the response time of the oxygen sensor.

FIG. 2 illustrates the relationship between the amount of iron contained in the coating 20 of the oxygen sensor and the response time Tr of the sensor. The amount of iron is calculated from the amount of ferric oxide used for the coating 20. As seen from FIG. 2, the response time Tr of the oxygen sensor is shorter when the iron content of the coating 20 falls within the range of 2% to 14% by weight. In other words, the water gas reaction can be promoted most when the iron content is in this range.

The coating 20 is further coated with a protective layer, though not illustrated in FIG. 1. The protective layer is made of a porous ceramic material such as spinel, alumina, etc.

The function of the above-described oxygen sensor will now be described.

During acceleration or high-load operation of the engine, the air-fuel ratio of a mixture supplied to the engine is changed to a rich side, and the amount of exhaust gas increases correspondingly. In this case, a large amount of carbon monoxide is contained in the exhaust gas which is liable to be absorbed to the surface of the second electrode 16 through the protective layer and the coating 20. However, because the coating 20 contains a catalyst which promotes the water gas reaction, as mentioned above, carbon monoxide that is being attracted to the second electrode 16 is changed to a carbonic acid gas due to the water gas reaction expressed by the aforesaid formula. Accordingly, the amount of carbon monoxide absorbed to the surface of the second electrode 16 can be reduced, and the formation of a film that hinders the passing of oxygen molecules can be suppressed.

When the air-fuel ratio of the mixture once changes to a rich side and then to a lean side, such a change to the lean side can be immediately detected by the oxygen sensor. This is because, when the air-fuel ratio of the mixture changes from a rich side to a lean side, the formation of a carbon monoxide film is suppressed. Therefore oxygen molecules in the exhaust gas can easily reach the surface of the second electrode 16 and the oxygen concentration of the exhaust gas can be detected accurately.

Since a change of the air-fuel ratio from a rich side to a lean side can be quickly detected, as mentioned above, it is possible to avoid the situation where an excessively small quantity of fuel is supplied to the engine due to an erroneous operation of the fuel supply device. Accordingly, the occurrence of a lean spike can be avoided, and the amount of nitrogen oxides (NOx) in exhaust gases can be reduced.

The present invention is not limited to the above-described first embodiment. A second embodiment illustrated in FIGS. 3 and 4 may alternatively be employed. In an oxygen sensor illustrated in FIG. 3, like reference numerals are used to indicate elements having the same function as the corresponding elements in FIG. 1, and a description thereof is omitted. In the following paragraphs, only the distinguishing features will be described.

Figure 3:
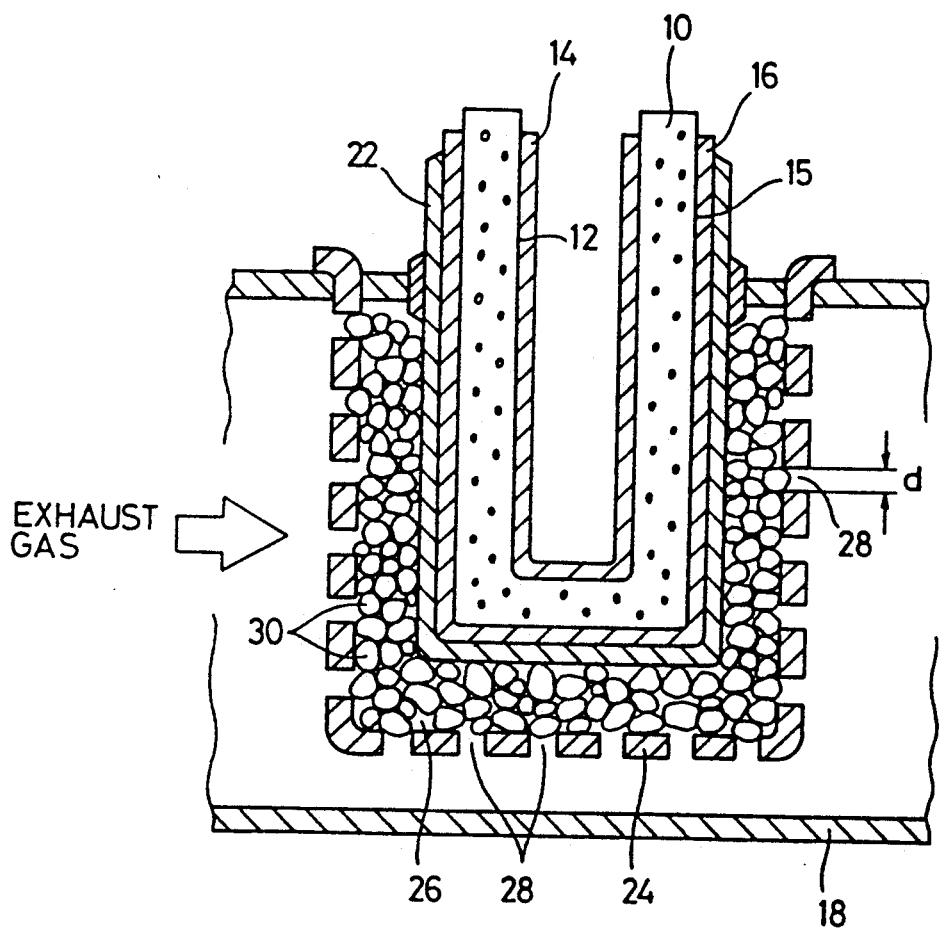
FIG. 3 is a schematic sectional view of an oxygen sensor according to a second embodiment of the invention.

In the oxygen sensor of FIG. 3, a protective layer 22, instead of the aforesaid coating 20, is coated over the surface of the second electrode 16. The protective layer 22 is, as explained in the first embodiment, made of a porous ceramic material such as spinel or alumina.

A portion of the hollow element 10 which protrudes into the exhaust pipe 18 is surrounded by a protective tube 24. The protective tube 24 is in the form of a cup closed at one end and open at the other end, and a chamber 26 is defined between the inner surface of the protective tube 24 and the protective layer 22. A large number of small holes 28 are bored through the protective tube 24 over the entire area thereof. Accordingly, the exhaust gas can pass through the small holes 28 of the protective tube 24 into the chamber 26 and then permeate through the protective layer 22 to the second electrode 16.

In this second embodiment, a large number of pellets 30, instead of the coating 20 of the first embodiment, are charged in the aforesaid chamber 26. The pellets 30 are composed of carrier made of alumina, etc., and the above-mentioned catalyst and promoters, for example. The particle diameter of the pellets 30 is greater than the diameter d of the small holes 28. If, however, the particle diameter is too large, large large spaces will be present between the pellets 30 when the pellets 30 are charged in the chamber 26. Therefore, the exhaust gas passed through the small holes of the protective tube 24 will not sufficiently contact the pellets 30 while permeating through the layer of the pellets 30 and the above-mentioned water gas reaction will not be satisfactorily induced. If, on the other hand, the particle diameter of the pellets 30 is too small, the diameter d of the small holes 28 of the protective tube 24 must also be small. However, the machining of such small holes 28 leads to an increase of the manufacturing cost of the oxygen sensor. When both the satisfactory occurrence of the water gas reaction and the manufacturing cost are taken into account, the diameter d of the small holes 28 is preferably set from 0.5 to 2.0 mm.

Figure 4:
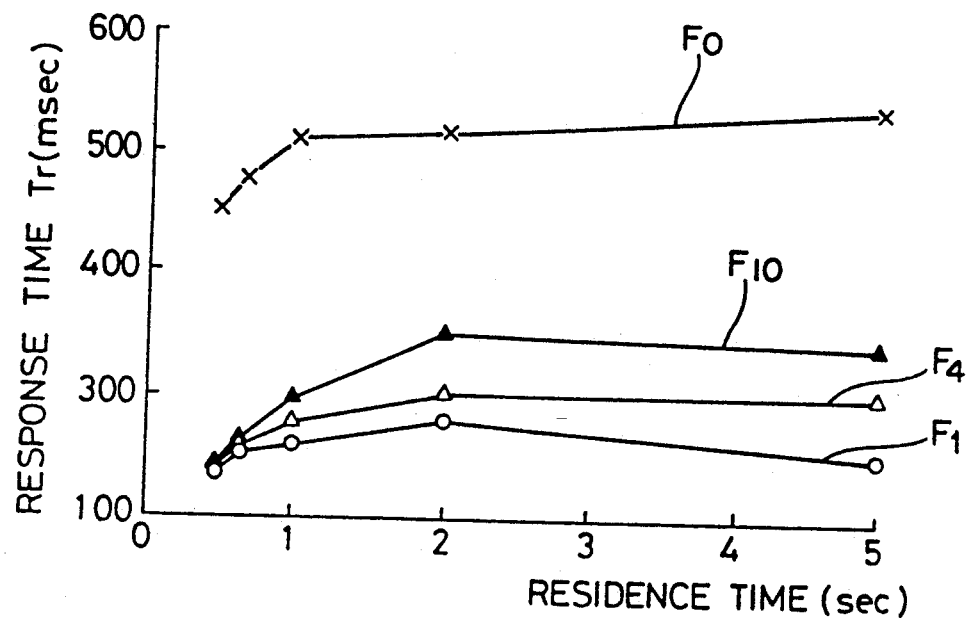
FIG. 4 is a graph illustrating the relationship between the amount of a catalyst contained in pellets as illustrated in FIG. 3 and the response time of the oxygen sensor.

FIG. 4 illustrates the relationship between the response time Tr of the oxygen sensor, where the pellets 30 contain ferric oxide as the catalyst, and the amount of iron contained in the layer of the pellets 30, where the amount of iron is calculated from the amount of ferric oxide contained in the layer of the pellets 30. Similar to the graph of FIG. 5, the residence time of the enriched state and the response time Tr are indicated respectively along the abscissa and the ordinate of FIG. 4. In FIG. 4, a characteristic curve F0 illustrates the case where pellets containing 5 g of iron per liter are used, and characteristic curves F1, F4, and F10 illustrate the cases where pellets containing 1 g, 4 g, and 10 g of iron per liter are used, respectively.

As seen from FIG. 4, the presence of ferric oxide as the catalyst in the layer of the pellets 30 contributes to the reduction in the response time Tr of the oxygen sensor. Particularly, when the amount of iron calculated from the amount of ferric oxide in the pellets layer is not greater than a predetermined value, preferably, when the amount is not greater than 10 g per liter, the response time Tr of the oxygen sensor can especially be shortened. This is because, as explained with reference to the first embodiment, the water gas reaction occurs when the exhaust gas passes through the layer of the pellets 30. Accordingly, the amount of carbon monoxide absorbed into the second electrode 16, i.e., positioning due to carbon monoxide, can be reduced.

As illustrated in FIG. 4, when the amount of ferric oxide as the catalyst, i.e., the amount of iron contained in the layer of the pellets 30, is increased, the response time Tr of the oxygen sensor becomes greater. This phenomenon is caused presumably for the following reason.

When preparing the above-mentioned catalyst, it is difficult to obtain a catalyst consisting solely of ferric oxide; the actually produced catalyst usually contains ferric oxide as a major component and a small quantity of ferrous oxide (FeO). Ferrous oxide combines with oxygen in the exhaust gas to form ferric oxide, according to the following formula.

$$2FeO + (\tfrac{1}{2})O_2 \rightarrow Fe_2O_3$$

Accordingly, when the air-fuel ratio of a mixture changes from a rich side to a lean side, oxygen in the exhaust gas is consumed by the reaction expressed in the above formula. Thus, the change of the air-fuel ratio from the rich to lean side cannot be quickly detected, and the response time Tr of the oxygen sensor becomes greater. It is therefore necessary that the carbon monoxide in the exhaust gas should be well subjected to the water gas reaction by ferric oxide as the catalyst and the reaction of the above formula should be suppressed. Taking these conditions into account, the amount of iron calculated from the amount of ferric oxide contained in the pellet layer should preferably be not greater than 10 g per liter.

The above-described oxygen sensor of the second embodiment has advantages similar to those of the oxygen sensor of the first embodiment.

In the foregoing embodiments, oxygen sensors are described which detect the oxygen concentration of an exhaust gas of a motor vehicle, but the oxygen sensor of the invention can of course be used to detect the oxygen concentration of an exhaust gas from a boiler, furnace, and the like.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An oxygen sensor for detecting an oxygen concentration of a detected gas containing carbon monoxide, comprising:
    a solid electrolyte element capable of conducting oxygen ions, said element having a first surface exposed to a reference gas of a constant oxygen concentration and a second surface exposed to the detected gas;
    electrode means for detecting an electromotive force produced between said first and second surfaces of said element in response to a difference in the oxygen concentration between the detected gas and said reference gas, said electrode means having a first electrode disposed on said first surface of said element and a second electrode disposed on said second surface of said element; and
    catalyst means at said second electrode for causing and promoting a water gas reaction involving the carbon monoxide contained in the detected gas approaching said second electrode which produces $CO_2$ and $H_2$ as a result of a chemical combination of the carbon monoxide and $H_2O$ in a gaseous state of the detected gas for reducing the carbon monoxide content and increasing the $H_2$ content in the detected gas so that the carbon monoxide is prevented from contaminating said second electrode by promoting the water gas reaction;
    said catalyst means includes a coating formed on the surface of said second electrode, said coating containing a catalyst for promoting said water gas reaction and comprising a heat-resistant inorganic material including ferric oxide as said catalyst in an amount such that the calculated amount of iron in said coating is within a range of 2% to 14% by weight.

2. The oxygen sensor according to claim 1, wherein said coating further contains a promoter for activating a catalytic action.

3. The oxygen sensor according to claim 2, wherein said promoter contains at least one of chromium oxide and potassium carbonate.

4. A solid electrolyte element for detecting an oxygen concentration of a detected gas containing carbon monoxide, said element being capable of conducting oxygen ions and having a first surface exposed to a reference gas of a constant oxygen concentration and a second surface exposed to the detected gas, comprising:
    an electrode disposed on said second surface of said element; and
    catalyst means at said electrode for causing and promoting a water gas reaction involving the carbon monoxide contained in the detected gas approaching said electrode which produces $CO_2$ and $H_2$ as a result of a chemical combination of the carbon monoxide and $H_2O$ in a gaseous state of the detected gas for reducing the carbon monoxide content and increasing the $H_2$ content in the detected gas so that the carbon monoxide is prevented from contaminating said electrode by promoting the water gas reaction;
    said catalyst means comprises a coating including a catalyst for promoting said water gas reaction, said coating comprises a heat-resistant inorganic material including ferric oxide as said catalyst in an amount such that the calculated amount in said coating is within a range of 2% to 14% by weight.

5. The solid electrolyte element according to claim 4, wherein said coating further comprises a promoter for activating a catalytic action.

6. The solid electrolyte element according to claim 5, wherein said promoter comprises chromium oxide and/or potassium carbonate.

7. A method for preventing contamination by carbon monoxide in an oxygen sensor which detects an oxygen concentration of an exhaust gas containing carbon monoxide comprising the steps of:
    receiving a portion of the exhaust gas at an electrode of the oxygen sensor; and
    causing and promoting a water gas reaction involving the carbon monoxide contained in the exhaust gas approaching said electrode by catalyst means which produces $CO_2$ and $H_2$ as a result of a chemical combination of the carbon monoxide and $H_2O$ in a gaseous state of the detected gas for reducing the carbon monoxide content and increasing the $H_2$ content in the detected gas so that the carbon monoxide contained in the exhaust gas is prevented from contaminating said electrode by promoting the water gas reaction by providing a coating on said electrode comprising a catalyst of a heat-resistant inorganic material for promoting said water gas reaction including an amount of ferric oxide such that a calculated amount of iron in said coating is within a range of 2% to 14% by weight.

* * * * *